(12) United States Patent
Pfeifer

(10) Patent No.: US 10,436,689 B2
(45) Date of Patent: Oct. 8, 2019

(54) TEST PENDULUM ARRANGEMENT AND METHOD FOR OPERATING A TEST PENDULUM ARRANGEMENT

(71) Applicant: Gerhard Pfeifer, Johannesberg (DE)

(72) Inventor: Gerhard Pfeifer, Johannesberg (DE)

( * ) Notice: Subject to any disclaimer, the term of this patent is extended or adjusted under 35 U.S.C. 154(b) by 0 days.

(21) Appl. No.: 15/576,161

(22) PCT Filed: May 19, 2016

(86) PCT No.: PCT/DE2016/000212
§ 371 (c)(1),
(2) Date: Nov. 21, 2017

(87) PCT Pub. No.: WO2016/184449
PCT Pub. Date: Nov. 24, 2016

(65) Prior Publication Data
US 2018/0136077 A1    May 17, 2018

(30) Foreign Application Priority Data

May 21, 2015   (DE) .................. 10 2015 006 594

(51) Int. Cl.
*G01N 3/30*   (2006.01)
*G01L 5/00*   (2006.01)
*G01M 7/08*   (2006.01)

(52) U.S. Cl.
CPC .............. *G01N 3/30* (2013.01); *G01L 5/0052* (2013.01); *G01M 7/08* (2013.01)

(58) Field of Classification Search
CPC ...... G01L 5/0052; G01L 5/0066; G01L 25/00

USPC ... 73/1.08, 1.39, 12.01, 12.04, 12.09, 865.9, 73/866.4
See application file for complete search history.

(56) References Cited

U.S. PATENT DOCUMENTS

| 1,682,138 A | * | 8/1928 | Merrill .................... G01M 9/00 73/147 |
| 5,922,937 A | | 7/1999 | Kowalski et al. |
| 2005/0204800 A1 | | 9/2005 | Yetukuri et al. |
| 2013/0047700 A1 | * | 2/2013 | Bonathan ................ G01N 3/30 73/12.04 |

FOREIGN PATENT DOCUMENTS

| CN | 202757749 U | 2/2013 |
| DE | 102011100370 A1 | 11/2012 |

(Continued)

OTHER PUBLICATIONS

Gruss; Christian; International Search Report; 4 pages; PCT/DE2016/000212; dated Sep. 23, 2016.

*Primary Examiner* — Benjamin R Schmitt
(74) *Attorney, Agent, or Firm* — Nexsen Pruet, LLC; Todd A. Serbin

(57) ABSTRACT

The invention relates to a test pendulum arrangement for carrying out a crash test dummy certifications, having a test probe which is arranged suspended on a cable arrangement, wherein test conditions are standardized and a cable standard length ($l_N$) is provided, the cable arrangement having a suspension, wherein a first drive for accelerating the test probe and at least a second drive for displacing the suspension are provided. The invention also relates to a method for operating a corresponding test pendulum arrangement.

20 Claims, 3 Drawing Sheets

(56) References Cited

FOREIGN PATENT DOCUMENTS

| | | |
|---|---|---|
| DE | 102014002526 A1 | 8/2015 |
| EP | 2098850 A2 | 9/2009 |
| FR | 2839636 A1 | 11/2003 |
| JP | 2005017165 A | 1/2005 |

* cited by examiner

TEST PENDULUM ARRANGEMENT AND METHOD FOR OPERATING A TEST PENDULUM ARRANGEMENT

RELATED APPLICATIONS

This application is a U.S. national phase application, claiming priority under 35 U.S.C. 371 to PCT application PCT/DE2016/000212, filed on May 19, 2016, claiming priority to German national application 10 2015 006 594.7, filed on May 21, 2015, the contents of the these applications incorporated by reference as if fully set forth herein in their entirety.

FIELD AND BACKGROUND OF THE INVENTION

Crash test dummies are used in the automotive industry to test the safety of motor vehicles regarding occupant protection in the event of an accident. For this purpose, different standardized crash tests are carried out, for example frontal impacts, side impacts, rear impacts and rollover tests. The crash test dummies are mounted or otherwise positioned in motor vehicles to be tested, and respective crash tests are carried out.

The used crash test dummies have a plurality of sensors in order to be able to measure the effect of the crash on the crash test dummy. In many cases, the used sensors are force sensors, position transducers and acceleration sensors. While carrying out the crash test, these sensors measure and record occurring accelerations, penetrations and forces. The measuring data subsequently are evaluated and the strain is analyzed.

The crash test dummies are to simulate the characteristics of humans. This is in reference to dimensions, flexibility, weight and the like. For this reason, crash test dummies are difficult to handle.

A crash test dummy is regularly certified so to ensure that it returns reliable values. For the certification, the measurement chain made of mechanics sensors of the crash test dummies has to be tested. For this purpose, a plurality of different tests are necessary.

Some of the tests provide that a test pendulum, which has a defined mass and which is suspended at a defined length from a cable assembly, is swung from a defined height against predetermined points of the crash test dummy. Such predetermined points, for example, are situated at the hips, shoulders, sternum and head. The pendulum on impact has, on account of the known mass and the precisely defined movement of the pendulum, a precisely determined pulse. This precision is used to test the reaction of the sensors of the crash test dummy in response to the precisely determined pulse. If a sensor outputs a value which is not within a narrow limit value corridor, a defect of the sensor or of the mechanical components of the crash test dummy is indicated, and the respective sensor or the defective mechanical components are replaced. The certification of the crash test dummies ensures that the measuring system delivers correct values for the crash test dummy, with the aid of which the vehicle approval tests can be carried out and the targeted development of corresponding restraint systems is enabled.

Conventional certification devices, which work with the test pendulums described previously, are constructed around the test pendulum. As a function of the respective test to be carried out, the crash test dummy has to be positioned precisely in relation to a reference point determined by the test pendulum. For spaces having a low ceiling clearance, as a result, the height of the reference point is located in an ergonomically disadvantageously low manner. On account of the characteristics of the crash test dummy, the size, the articulated extremities and the high weight of most crash test dummies, in particular of adult-size crash test dummies, this task is physically very demanding for the personnel carrying out the tests. Furthermore, for the certification of one individual test crash dummy, a plurality of test rounds have to be performed at the test pendulum, so that a crash test dummy for a certification has to be newly positioned numerous times. The positioning has to be carried out with much precision in relation to the reference point. This task is time consuming, so that each day only a small number of certifications can be performed. Moreover, the crash test dummies when being certified are not available for carrying out crash tests. The operation of a certification lab is necessary; however, it is uneconomical.

The test devices necessary for the certification of crash test dummies, in particular the pendulums to be used, take up a lot of space because the standardized cable length is great and the pendulum has to be deflected by a great amount. For this reason, construction and operation of respective devices for crash test dummies are associated with complications. On the one hand, sufficiently sized rooms have to be provided; on the other hand, the facilities when in operation have to be protected against accidents, in particular collisions including swinging test pendulums.

BRIEF DESCRIPTION OF THE DRAWINGS

Schematically.

DESCRIPTION OF EMBODIMENTS OF THE INVENTION

Figure 1:
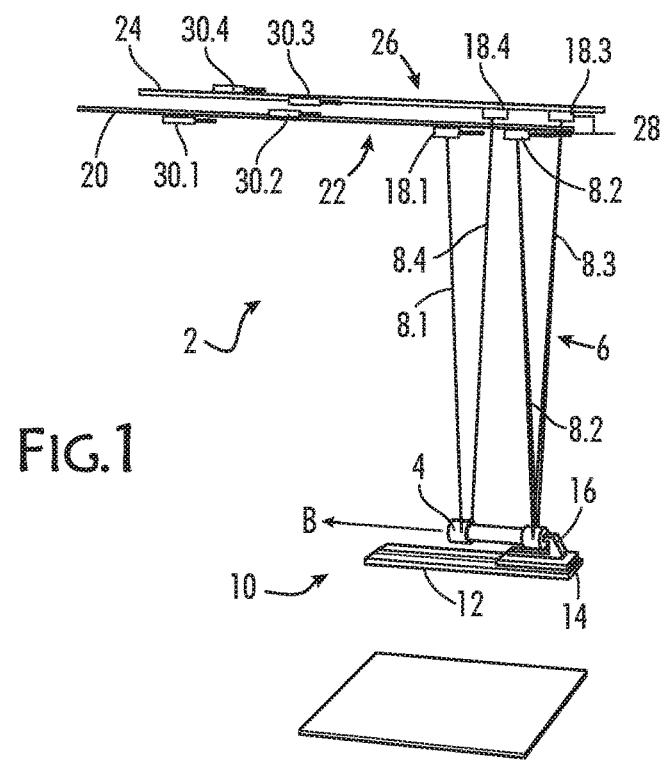
FIG. 1 shows a test pendulum arrangement according to a first embodiment.

In the following, a test pendulum arrangement and a method for operating the test pendulum arrangement are described. The test pendulum arrangement serves the certification of crash test dummies and has a test probe, which is hangingly disposed at a cable assembly.

An object of the present invention is to further develop test pendulum arrangements and a method for operating test pendulum arrangements of the kind mentioned at the outset, so that the space required to set up and operate a respective test pendulum arrangement is reduced and so that the operating safety of corresponding test pendulum arrangements may be established with a smaller outlay.

The object is achieved by a test pendulum arrangement according to claim 1 and by a method for operating a test pendulum arrangement according to other independent claim 12. Further embodiments of test pendulum arrangements and of the method for operating the test pendulum arrangement are the subject of the dependent claims.

Subsequently, a test pendulum arrangement for carrying out a crash test dummy certification is described, which has a test probe hangingly disposed at a cable assembly. The test requirements for carrying out the crash test dummy certification are standardized. The standardization serves to ensure the introduction of a precisely defined pulse into the crash test dummy, so that the values recorded by the sensor system of the crash test dummy can be related to a specified value, the introduced pulse. Among other things, the standardized test requirements provide a standard cable length. In conjunction with the also standardized features of the test probe, a pulse which is within very narrow tolerances is thus determinable and, for this reason, allows for a certification of the crash test dummy.

The cable assembly has a suspension, at which cables of the cable assembly are fixed above the test probe.

The test pendulum arrangement has a first actuator for accelerating the test probe. By using a first actuator for accelerating the test probe, the acceleration distance necessary for reaching a specified velocity of the test probe at the point of impact of the crash test dummy is shortened. This reduces the space required for mounting and operating a respective test pendulum arrangement. Moreover, the shortened acceleration distance enables a considerable reduction of the risk of collision with the operating personnel, because the potential space for collision, in which the test probe and the personnel can collide, is smaller.

Furthermore, at least one second actuator is provided for moving the suspension. With the aid of at least one second actuator, the suspension can be moved together with the test probe. In so doing, it can be achieved that the cable assembly consistently has the same cable tension while accelerating the test probe. As a result, oscillations of the pendulum perpendicular to the desired direction of movement can be prevented. Moreover, the test probe in this way may be linearly accelerated, because the distance between pendulum and suspension may be kept at a constant level. An acceleration of the pendulum on a circular path, which, for example, might be required in the case of a fixed suspension of the cable assembly, can thus be prevented. An acceleration on a circular path would render the configuration of a first actuator more complex and more expensive. With the aid of the respective test pendulum arrangement, the required pulse of the test probe may be achieved with high precision in a much smaller space than previously and without side effects such as vibrations in the cable assembly or the like.

In a first further embodiment of the test pendulum arrangement, an open loop control or a closed loop control may be provided, which serves to actuate the first actuator and the at least one second actuator. With the aid of a respective open loop control or a closed loop control, the first actuator and the at least one second actuator thus may be synchronized. It is furthermore possible to use different test probes which, for example, may have different masses or different contours, because an open loop control or a closed loop control is able to take into account corresponding parameters when actuating the actuators.

The open loop control enables a free definition of the pivot point of the cable suspension. This furthermore allows for omitting the possibility of a horizontal positioning of the crash test dummy vis-à-vis a reference point and, instead, the point of impact of the dummy is contacted and processed from the control side using the actuator.

According to a further aspect of the present invention, the connection between test probe and cable assembly may be releasable. In this instance, different closure systems may be provided, for example quick acting closures.

In a different further embodiment, the first actuator and/or the at least one second actuator may be linear actuators. Linear actuators are very efficient and allow for accelerating high masses over short distances. For this reason, linear actuators can be quickly decelerated, which results in a precise replicability of the standardized test requirements. The use of linear actuators enables the further shortening of the necessary acceleration distances. As a result, the space requirements and, for this reason, the accident risk are further reduced.

The linear actuators of the cable suspension may, in particular, be designed as iron-free linear motor actuators, which may have slides guided on track rails. These slides feature low masses and, for this reason, minimize the masses to be accelerated and decelerated.

In one possible embodiment, the first linear actuator for the test probe may be configured as a linear motor appended with iron or as a toothed belt axis having a servo drive. These actuators are significantly more efficient; however, they are also less dynamic than iron-free linear motors. Since a precise stopping point for the acceleration of the test probe is not required, this factor has no practical relevance.

Alternatively or additionally to the linear actuators, other actuators may be used, for example servo drives and/or ball screw actuators.

In a different further embodiment, it can be provided that the cable assembly has at least four cables to which the test probe is fastened. Viewed in the direction of acceleration, the cables can set up a V, as a result of which the centering of the test probe can be achieved and a propensity for swinging laterally is reducible.

In a view transverse to the direction of acceleration of the test probe, the cables can be parallel, as a result of which the test probe can be guided onto a circular path. The distance of the suspension transverse to the direction of acceleration can equal to the distance of the suspension points of the cables at the test probe. Consequently, circular paths offset in a parallel manner result as trajectories of the cables, and a clean guiding of the test probe is possible.

For the first track and for the second track, respectively one actuator rail, in particular a rail of a linear actuator, may be provided. As a result, the quantity of actuators required for the suspension is reduced.

A further aspect of the present invention may provide that the cable assembly has at least six cables, at least three cables being disposed in a first track and at least three cables being disposed in a second track, and at least two of the six cables are disposed in an intersecting manner at the test probe.

Thus, in some embodiments, four cables can be disposed at a front suspension or at a rear suspension of the test probe. In other embodiments, eight cables can be provided, so that four cables are disposed at a front suspension of the test probe and four cables are disposed at a rear suspension of the test probe.

With the aid of six cables or more, of which at least two are disposed in an intersecting manner, a rolling of the test probe about its longitudinal axis is prevented.

A yet further aspect of the present invention provides that each cable has its own suspension.

According to a further embodiment, when at least six cables are used, it can be provided that at least two cables of the first track and two cables of the second track are disposed at a common suspension.

A further aspect of the present invention provides that each suspension has its own actuating slide. By providing individual actuating slides for each suspension, the to-be-accelerated masses of the suspensions may be minimized, increasing the precision of the actuator. Furthermore, a variable axial distance of the test probe may be adjusted and test probes already present and having different distances may be continuously used without adaptations.

According to a further embodiment, shock absorbers, in particular hydraulic shock absorbers, may be provided at the actuation rails. As soon as no further acceleration of the test probe is required, the shock absorbers may take over the deceleration of the actuating slides.

In a further refinement of the aforementioned embodiment, each actuating slide may have a position sensor, so that a closed loop control always receives feedback about the current position of each actuating slide, as a result of which the precision of the test pendulum arrangement when operated may be further increased.

Another further aspect of the test pendulum arrangement provides that the cable assembly has a cable length which corresponds to a fraction of the standardized cable length. The fraction may be a proper fraction or an improper fraction.

When using more than four cables, the aforementioned cable length does not refer to cables guided in an intersecting manner.

By providing at least two actuators, shorter cable lengths can also be used as the standard cable length, reducing the space required between a cable suspension and the point of impact of the test probe in the vertical direction. The respective test laboratories, in which the test pendulum arrangement described here may be used, for this reason can have lower ceiling heights than test laboratories for known test pendulum arrangements, facilitating the setup of respective certification laboratories. Thus, the test probe can always be situated in an ergonomic working height.

Within the scope of this embodiment, the at least one second actuator can be actuated in such a manner that a cable movement of a cable in standard length can be simulated for a specific suspension point. This cable movement can be determined from the known velocity of the test probe at the point of impact with the aid of the intercept theorem.

In another further embodiment, the first actuator may have a releasable connection to the test probe, so that the test probe is decoupleable from the first actuator. In so doing, the test probe may be released from the first actuator before striking the crash test dummy. At the moment of impact, the test probe swings freely and in a manner conforming to standards.

In a further possible embodiment, a cable connection between the first actuator, in particular a slide, and the test probe may be provided. The length of the cable is dimensioned in such a manner that it allows at least one unhindered first impact onto the crash test dummy; however, it stops the test probe when reversing the actuating slide. This eliminates endangering an operator by a diverted swing of a test probe after impact onto the crash test dummy and it prevents damage to the testing device if a test is not carried out according to specifications, for example, without a crash test dummy.

A first independent subject described here relates to a method for operating a test pendulum arrangement according to the type described before. In so doing, it is provided that the test probe with the aid of the first actuator and the suspension with the aid of the at least one second actuator are accelerated with respectively equal accelerations starting from the resting state, the suspension being decelerated and the test probe being decoupled from the first actuator, so that the test probe swings freely. In this manner, it is possible to precisely accelerate the test probe in the same way as a classic test pendulum arrangement; however, the space requirements are significantly smaller. In particular when using linear actuators, high positive and negative accelerations can be achieved, so that tolerances specified by the standard may be adhered to.

According to one embodiment, the coupling device may be constructed identical for all test probes. The coupling device may be retrofittable for existing probes.

In a first further embodiment of the method, the suspension, after decoupling the test probe, can be moved by a velocity of:

$$v_A = v_P * \left(1 - \frac{l_P}{l_N}\right).$$

In this instance, $v_A$ equals the velocity of the suspension, $v_P$ equals the velocity of the test probe at the point of impact, $l_P$ equals the actual length of the cable and $l_N$ equals the standard length of the cable.

If the actual length of the cable $l_P$ equals the standard length of the cable $l_N$, the velocity of the suspension point equals 0. When the standard length of the cable is halved, the velocity of the suspension has to equal half of the velocity of the test probe. According to a further aspect of the method, it may be provided that the first actuator after decoupling the test probe is moved in an opposite direction of the acceleration. As a result, damage to the releasable connection of the first actuator for the test probe by a test probe swinging backwards may be prevented.

After a first impact with the crash test dummy, the complete test pendulum arrangement may be moved back to a position at a distance from the crash test dummy to so prevent a second impact onto the crash test dummy which usually has fallen over.

Further objects, features and advantageous possibilities for application of the present invention result from the subsequent description of an exemplary embodiment on the basis of the drawings. In this instant, all described and/or illustrated features in meaningful combination form the subject of the present invention, even irrespective of the patent claims and their back references.

In the subsequent exemplary embodiments, the same components or components having the same effect are denoted with the same reference characters for better readability.

FIG. 1 shows a perspective view of a test pendulum arrangement 2 according to a first embodiment.

Test pendulum arrangement 2 has a test probe 4, which is fixed to a cable assembly 6.

Cable assembly 6 has four cables 8.1 through 8.4. Viewed from an acceleration direction B, cables 8.1 and 8.4 and cables 8.2 and 8.3 span respectively one V. Cables 8.1 through 8.4 are respectively fixed to test probe 4. The cables respectively have a standard length $l_N$.

Test probe 4 is disposed at a first linear actuator 10. Linear actuator 10 has a track rail 12 and a slide 14 guided on track rail 12. At slide 14, a wedge 16 is situated, at which test probe 4 abuts. If slide 14 is accelerated in acceleration direction B, wedge 16 acts together with test probe 4 and accelerates test probe 4.

Cables 8.1 through 8.4 at their upper end are fixed to suspensions, which are configured respectively as actuating slides 18.1 through 18.4. Actuating slides 18.1, 18.2 run on a first actuator rail 20 of a linear actuator 22. Actuating slides 18.3, 18.4 run on a second actuator rail 24 of a linear actuator 26. Linear actuators 10, 22 and 26 or actuating slides 14 and 18.1 through 18.4 are controlled by closed loop control 28. Instantaneous location information of respective actuating slides 14 and 18.1 through 18.4 are transmitted to closed loop control 28. As a result, a precise position-time control can be performed.

In other embodiments, instead of different actuating slides, one actuating slide may be provided for each track rail 20, 24.

In the illustrated embodiment, hydraulic shock absorbers 30.1 through 30.4, which are disposed at actuator rails 20, 24, take over the deceleration of actuating slides 1.8.1 through 18.4. In this instance, respectively one individual shock absorber 30.1 through 30.4 is assigned to each actuating slide 18.1 through 18.4.

Actuating slides 18.1 through 18.4 may be configured in such a manner and shock absorbers 30.1 through 30.4 may be disposed in such a manner that respectively only one shock absorber 30.1 through 30.4 acts together with respectively only one actuating slide 18.1 through 18.4. For example, this may be realized via corresponding protrusions at actuating slides 18.1 through 18.4.

Figure 2:
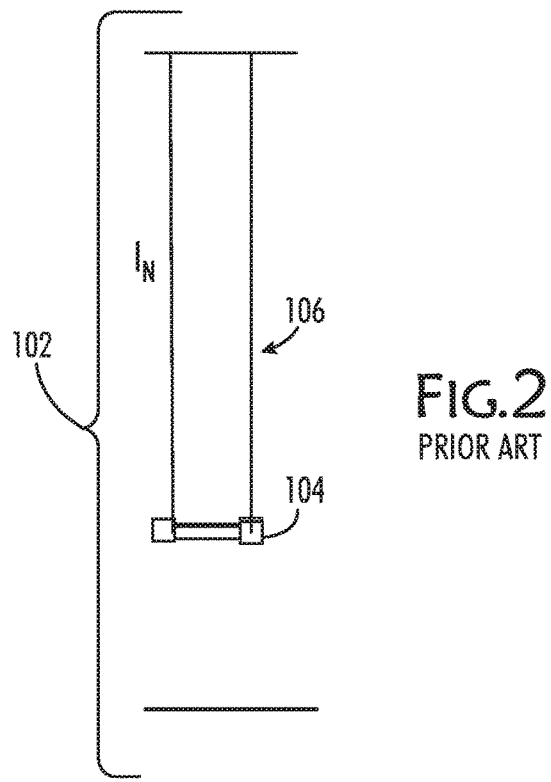
FIG. 2 shows a conventional test pendulum arrangement from the prior art.

FIG. 2 shows a test pendulum arrangement 102 from the prior art.

A test probe 104 is disposed at a cable assembly 106 having a standard length $L_N$. When the cables of cable assembly 106 are tightened, test probe 104 is elevated to a specified height and is released for carrying out the test. Test probe 104 is accelerated by gravity and it reaches, at the shown point of time at which a collision with the body to be tested is to occur, its specified velocity which, on account of the length of the cable and the predetermined height of the pendulum, is always equal.

Figure 3:
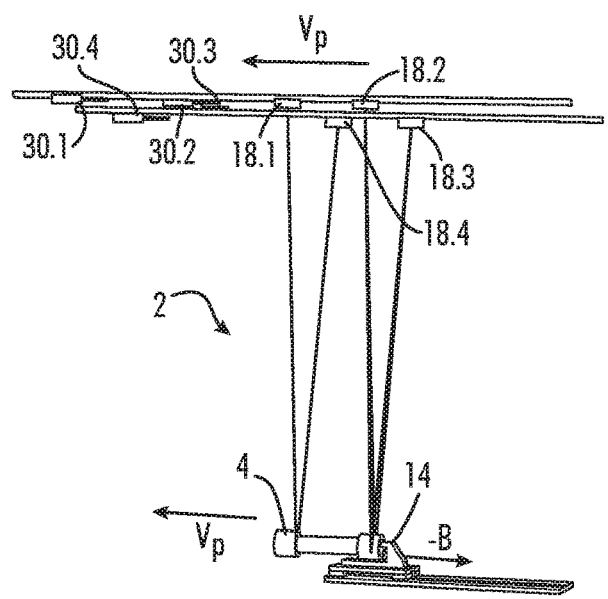
FIG. 3 shows the test pendulum arrangement from FIG. 1 at the time of releasing the test probe.

FIG. 3 show the test pendulum arrangement 2 from FIG. 1 at a point of time after the releasing.

In contrast to FIG. 1, test probe 4 has been released from slide 14 and moves in the forward direction at a velocity $v_P$. Actuating slides 18.1 through 18.4 move at the same velocity in the forward direction up to a point of impact of test probe 4. At the point of time of releasing, test probe 4 has the same kinetic condition as test probe 104 in FIG. 2. In order to accelerate test probe 4, however only a fraction of the space necessary to accelerate test probe 104 has been used. The space traveled by test probe 4 is significantly smaller than the space traveled by test probe 104 from the prior art so that the risk of collision of test probe 4 with the operating personnel is reduced.

Actuating slide 14 is accelerated counter to acceleration direction B, which equals the velocity vector $v_P$ of the test probe, so to avert a collision of test probe 4 after bouncing off a crash test dummy (not shown) and to thereby avert the risk of damage.

Figure 4:
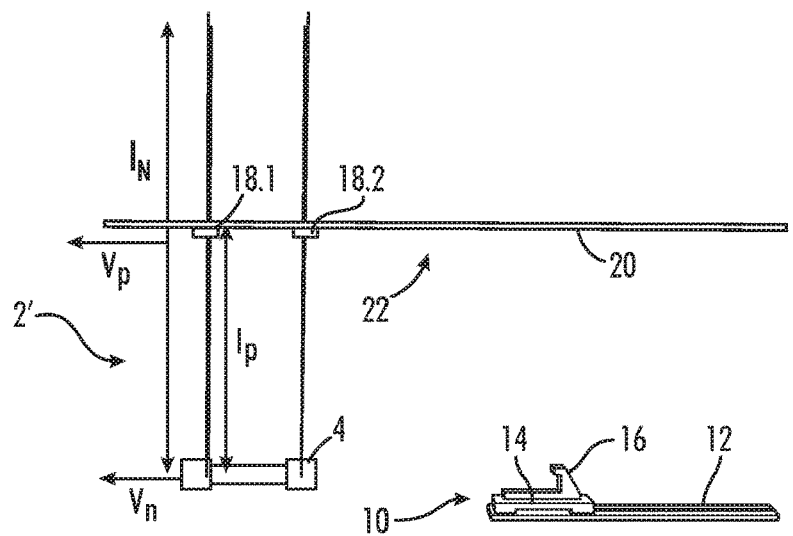
FIG. 4 shows a second embodiment of a test pendulum arrangement having a reduced cable length; and, FIG. 5 shows a test pendulum arrangement according to a third embodiment.

FIG. 4 shows a second embodiment of a corresponding test pendulum arrangement 2'.

Test pendulum arrangement 2' has a cable length $L_P$, which is smaller than standard cable length $L_N$ of test pendulum arrangement 2 from FIGS. 1 and 2.

When test pendulum arrangement 2' is operated, suspensions or actuating slides 18.1 through 18.4 are not decelerated to 0, but correspond with the intercept theorem in such a manner that actuating slides 18.1 through 18.4 move so as would a cable having a standard length $l_N$ in the corresponding position. The velocity of actuating slides 18.1 through 18.4 thus results from:

$$v_A = v_P * \left(1 - \frac{l_P}{l_N}\right).$$

In this way, the movements of a cable having a standard length may be exactly replicated.

Figure 5:
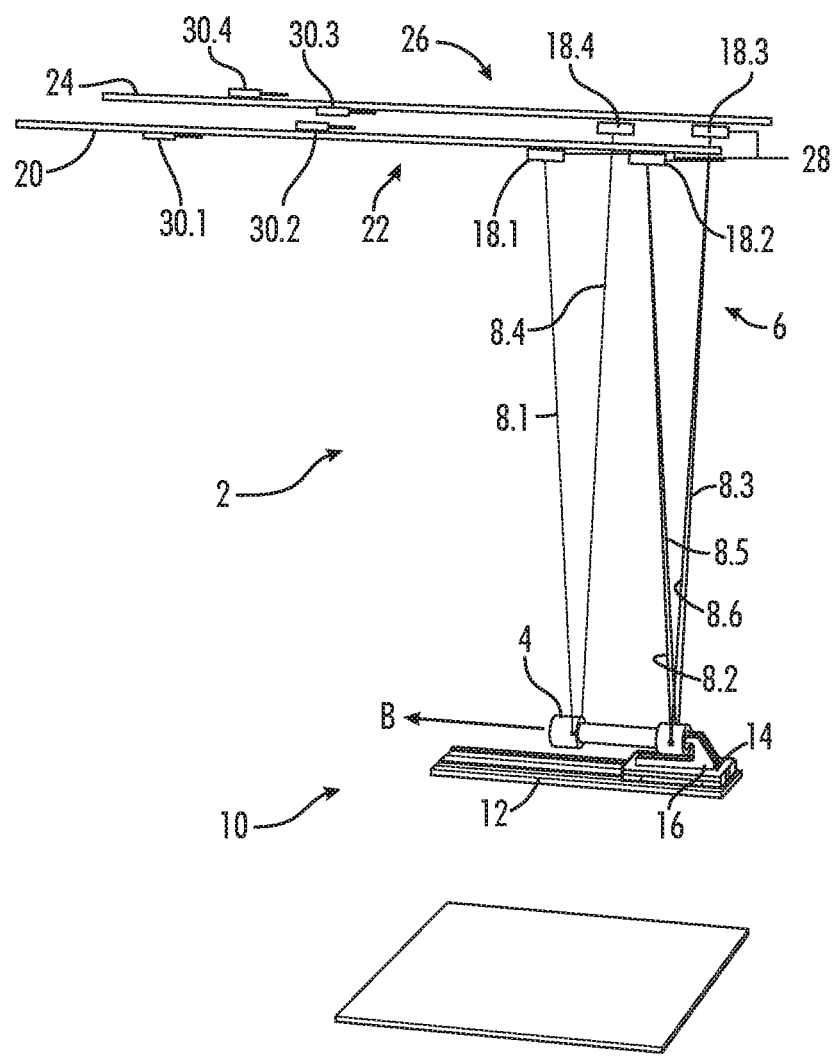

FIG. 5 shows a perspective view of a test pendulum arrangement 2'' according to a third embodiment.

Test pendulum arrangement 2 has a test probe 4, which is fixed to a cable assembly 6.

Cable assembly 6 has four cables 8.1 through 8.4. Viewed from an acceleration direction B, cables 8.1 and 8.4 and cables 8.2 and 8.3 span respectively one V. Cables 8.1 through 8.4 are respectively fixed to test probe 4. The cables respectively have a standard length $l_N$.

On the side facing away from acceleration direction B of test pendulum arrangement 2, two cables 8.5 and 8.6 are fixed in an intersecting manner at test probe 4, so that looking in acceleration direction B, cable 8.5 is guided from top left to bottom right and cable 8.6 is guided from top right to bottom left. Cables 8.5 and 8.6 prevent a rolling of test pendulum 2 about the longitudinal axis, which presently is positioned parallel to acceleration direction B.

Test probe 4 is disposed at a first linear actuator 10. Linear actuator 10 has a track rail 12 and a slide 14 guided on track rail 12. At slide 14, a wedge 16 is situated, at which test probe 4 abuts. If slide 14 is accelerated in acceleration direction B, wedge 16 acts together with test probe 4 and accelerates test probe 4.

Cables 8.1 through 8.6 at their upper ends are fixed to four suspensions, which are configured respectively as actuating slides 18.1 through 18.4. In this instance, cables 8.2 and 8.5 are fixed to actuating slide 18.2 and cables 8.3 and 8.6 are fixed to actuating slide 18.3. Actuating slides 18.1, 18.2 run on a first actuator rail 20 of a linear actuator 22. Actuating slides 18.3, 18.4 run on a second actuator rail 24 of a linear actuator 26. Linear actuators 10, 22 and 26 or actuating slides 14 and 18.1 through 18.4 are controlled by closed loop control 28. Instantaneous location information of respective actuating slides 14 and 18.1 through 18.4 are transmitted to closed loop control 28. As a result, a precise position-time control can be performed.

In the illustrated embodiment, hydraulic shock absorbers 30.1 through 30.4, which are disposed at actuator rails 20, 24, take over the deceleration of actuating slides 1.8.1 through 18.4.

In this instance, respectively one individual shock absorber 30.1 through 30.4 is assigned to each actuating slide 18.1 through 18.4.

Actuating slides 1.8.1 through 18.4 may be configured in such a manner and shock absorbers 30.1 through 30.4 may be disposed in such a manner that respectively only one shock absorber 30.1 through 30.4 acts together with respectively only one actuating slide 18.1 through 18.4. For example, this may be realized via corresponding protrusions at actuating slides 18.1 through 18.4.

What is claimed is:

1. A test pendulum arrangement for carrying out a crash test dummy certification, comprising:
   a test probe hangingly situated at a cable assembly, wherein a cable length ($l_N$) is provided,
   wherein the cable assembly comprises a suspension and at least four cables, wherein two cables are disposed in a first track and two cables are disposed in a second track, wherein respectively one actuator rail is provided for the first track and for the second track, and,
   wherein a first actuator for accelerating the test probe and at least one second actuator for moving the suspension are provided, wherein the suspension is configured as actuating slides.

2. The test pendulum arrangement as recited in claim 1, wherein an open loop control or a closed loop control for actuating the first actuator and the at least one second actuator is provided.

3. The test pendulum arrangement as recited in claim 1, wherein the first actuator and/or the at least one second actuator are linear actuators.

4. The test pendulum arrangement as recited in claim 1, wherein the cable assembly comprises at least six cables, wherein at least three cables are disposed in a first track and at least three cables are disposed in a second track, wherein at least two of the six cables are situated in an intersecting manner at the test probe.

5. The test pendulum arrangement as recited in claim 4, wherein at least two cables of the first track and two cables of the second track are disposed at a common suspension.

6. The test pendulum arrangement as recited in claim 5, wherein each suspension has its own actuating slide.

7. The test pendulum arrangement as recited in claim 1, wherein each cable has its own suspension.

8. The test pendulum arrangement as recited in claim 7, wherein each suspension has its own actuating slide.

9. The test pendulum arrangement as recited in claim 1, wherein shock absorbers are disposed at the actuator rails.

10. The test pendulum arrangement as recited in claim 1, wherein the cable assembly has a cable length ($l_p$), which corresponds to a fraction ($l_p/l_N$) of the cable length ($l_N$).

11. The test pendulum arrangement as recited in claim 1, wherein the first actuator comprises a releasable connection to the test probe, so that the test probe is decoupleable from the first actuator.

12. A method for operating a test pendulum arrangement including a test probe hangingly situated at a cable assembly wherein the cable assembly comprises a suspension and, where a first actuator for accelerating the test probe and at least one second actuator for moving the suspension are provided, comprising:
   accelerating the test probe in an acceleration direction (B) with the aid of the first actuator and the suspension with the aid of the at least one second actuator using respectively equal accelerations starting from the resting state;
   decelerating the suspension; and,
   decoupling the test probe from the first actuator so that the test probe swings freely.

13. The method as recited in claim 12, wherein the suspension after decoupling the test probe is moved at a velocity of $$v_A = v_P * \left(1 - \frac{l_P}{l_N}\right).$$

14. The method as recited in claim 12, wherein the first actuator after decoupling the test probe is moved counter to the acceleration direction (B).

15. A test pendulum arrangement for carrying out a crash test dummy certification, comprising:
   a test probe hangingly situated at a cable assembly, wherein a cable length ($l_N$) is provided, wherein the cable assembly comprises a suspension, and,
   wherein a first actuator for accelerating the test probe and at least one second actuator for moving the suspension are provided, wherein the suspension is configured as actuating slides, and
   wherein the first actuator and the at least one second actuator are linear actuators.

16. The test pendulum arrangement as recited in claim 15, wherein an open loop control or a closed loop control for actuating the first actuator and the at least one second actuator is provided.

17. The test pendulum arrangement as recited in claim 15, wherein the cable assembly comprises at least four cables, wherein two cables are disposed in a first track and two cables are disposed in a second track, wherein respectively one actuator rail is provided for the first track and for the second track.

18. The test pendulum arrangement as recited in claim 17, wherein each cable has its own suspension.

19. The test pendulum arrangement as recited in claim 18, wherein each suspension has its own actuating slide.

20. The test pendulum arrangement as recited in claim 15, wherein the cable assembly comprises at least six cables, wherein at least three cables are disposed in a first track and at least three cables are disposed in a second track, wherein at least two of the six cables are situated in an intersecting manner at the test probe.

* * * * *